(12) United States Patent
Kashida

(10) Patent No.: US 7,619,403 B2
(45) Date of Patent: Nov. 17, 2009

(54) METHOD FOR ELECTRICALLY DETECTING MOTION OF NONPOLAR COMPOSITE MOLECULE BY UTILIZING NONUNIFORM ELECTRIC FIELD

(75) Inventor: Shoji Kashida, Niigata (JP)

(73) Assignee: Niigata University, Niigata-Shi (JP)

( * ) Notice: Subject to any disclaimer, the term of this patent is extended or adjusted under 35 U.S.C. 154(b) by 273 days.

(21) Appl. No.: 11/574,312

(22) PCT Filed: Aug. 17, 2005

(86) PCT No.: PCT/JP2005/015018

§ 371 (c)(1),
(2), (4) Date: Feb. 26, 2007

(87) PCT Pub. No.: WO2006/025215

PCT Pub. Date: Mar. 9, 2006

(65) Prior Publication Data

US 2007/0273356 A1    Nov. 29, 2007

(30) Foreign Application Priority Data

Aug. 31, 2004    (JP) ............................ 2004-251840

(51) Int. Cl.
*G01N 27/00* (2006.01)
(52) U.S. Cl. .................................................. 324/71.1
(58) Field of Classification Search ............... 324/71.1, 324/658, 661, 662, 663, 686, 687, 688, 690, 324/695, 670, 671
See application file for complete search history.

(56) References Cited

U.S. PATENT DOCUMENTS 4,814,690 A * 3/1989 Melcher et al. ............. 324/674
5,208,544 A * 5/1993 McBrearty et al. .......... 324/687

(Continued)

FOREIGN PATENT DOCUMENTS

JP        3-502728 A    6/1991

(Continued)

OTHER PUBLICATIONS

Kakurai, et al., Dynamics of the strain-medicated phase transition in KDCO3: A thermal neutron spin-echo study, The American Physical Society, vol. 53, No. 10, pp. R5974-R5977, Mar. 1996.

(Continued)

*Primary Examiner*—Hoai-An D Nguyen
(74) *Attorney, Agent, or Firm*—Darby & Darby PC

(57) ABSTRACT

The conventional dielectric measurement method utilizes an interaction between a uniform electric field and a dipole moment, and hence a motion of nonpolar molecules without the dipole moments cannot be detected. It is an object of the present invention to provide a method for electrically detecting the motion of the nonpolar molecule. According to the present invention, the motion of the nonpolar molecule is detected electrically by utilizing a nonuniform electric field in dielectric measurement. As a specific measurement method, comb-shaped electrodes or electrodes with irregularities on their surfaces are employed in the dielectric measurement in place of conventional parallel flat-plate electrodes. By utilizing the interaction between the nonuniform electric field generated by these electrodes and a quadrupole moment or a high-order electric moment, it has become possible to electrically detect the motion of the nonpolar molecule.

8 Claims, 7 Drawing Sheets

U.S. PATENT DOCUMENTS

| | | | | |
|---|---|---|---|---|
| 5,454,472 | A | * | 10/1995 | Benecke et al. .......... 209/127.1 |
| 6,779,594 | B1 | * | 8/2004 | Judge et al. .................... 165/96 |
| 7,224,417 | B2 | * | 5/2007 | Angele et al. ................. 349/85 |
| 2004/0142409 | A1 | * | 7/2004 | Allen et al. ................... 435/29 |

FOREIGN PATENT DOCUMENTS

| | | | |
|---|---|---|---|
| JP | 6-502256 | A | 3/1994 |
| JP | 3029482 | B2 | 2/2000 |
| JP | 3195387 | B2 | 6/2001 |
| JP | 2002-536751 | A | 10/2002 |

OTHER PUBLICATIONS

Hamaguchi, Hiro-o, et al., "Raman Spectroscopy," Japan Scientific Societies Press, 1994.

Sakata, Ryou., "Solid-State Science," Baifukan Co., Ltd., 1989, p. 221.

Takashige, Masaaki., "Materials Structure and Introduction to Dielectric," Shokabo Publishing Co., Ltd., 2003, p. 46.

International Search Report dated Dec. 20, 2005 issued for corresponding International Patent Application No. PCT/JP2005/015018.

* cited by examiner

Carbonate Acid Molecule within Potassium Hydrogen Carbonate

Electrode with Irregularities on its Surface

METHOD FOR ELECTRICALLY DETECTING MOTION OF NONPOLAR COMPOSITE MOLECULE BY UTILIZING NONUNIFORM ELECTRIC FIELD

CROSS REFERENCE TO PRIOR APPLICATIONS

This is a U.S. national phase application under 35 U.S.C. § 371 of International Patent Application No. PCT/JP2005/015018 filed Aug. 17, 2005, and claims the benefit of Japanese Application No. 2004-251840 filed Aug. 31, 2004. The International Application was published in Japanese on Mar. 9, 2006 as International Publication No. WO 2006/025215 under PCT Article 21(2), the content of which is incorporated herein in its entirety.

TECHNICAL FIELD

The present invention relates to a method for electrically detecting a motion of a nonpolar molecule.

BACKGROUND ART

For analysis of molecular motions in solids, liquids and gases, dielectric measurement utilizing a uniform electric field is widely employed. In general, molecules can be classified into a polar molecule having no symmetry center but having an electric dipole moment, and a nonpolar molecule having a symmetry center but having no electric dipole moment. When permittivity of solid or liquid containing a polar molecule with a degree of freedom of internal rotation is measured as a function of frequencies by utilizing the conventional method for measuring an electric response of a substance under a uniform electric field, a graph shown in FIG. 10 is obtained. As shown in FIG. 10, a dielectric loss exhibits a peak and a permittivity then decreases at a critical frequency $f_c$ at which a molecular rotational motion becomes unable to follow a time change in alternate current. Thus, from the dielectric measurement data, information on the molecular motion can be obtained. According to the conventional measuring method utilizing a uniform electric field, it is possible to analyze a motion of a polar molecule having an electric dipole moment, whereas it is not possible to analyze that of a nonpolar molecule having no dipole moment.

In order to measure the motion and relaxation of a nonpolar molecule unresponsive to suchlike dielectric measurement, optical methods such as Raman scattering and neutron inelastic scattering method have been employed. The optical methods utilize visible light ($10^{14}$ Hz) and hence a relaxation phenomenon observable by the optical method is limited, thereby making it difficult to measure phenomena occurring at $10^{11}$ Hz or less. Besides, the neutron inelastic scattering method utilizes neutrons with the number of vibrations in the order of $10^{12}$ Hz, and hence, it is difficult for the current technologies to detect motions slower than those occurring at $10^{10}$ Hz or less due to energy resolution.

See, "Solid-State Science" by Ryou Sakata, published by Baifukan Co., Ltd. in 1989, p 221; "Materials Structure and Introduction to Dielectric" by Masaaki Takashige, published by "Shokabo Publishing Co., Ltd." in 2003, p 46; and "Raman Spectroscopy" edited by Hiro-o Hamaguchi and Akiko Hirakawa, published by "Japan Scientific Societies Press" in 1994.

The conventional method utilizing a uniform electric field is suitable to detect the motion of a polar molecule with the dipole moment. In nonpolar composite molecules where the dipole moments are combined with the polarities opposed to each other, however, forces acting on the dipole moments cancel each other to thereby permit no interaction to occur between the directions of the electric field and the molecular axes, thus making it impossible to detect the motion of the nonpolar molecule by the uniform electric field method. It is an object of the present invention to provide a method for electrically detecting a motion of such nonpolar composite molecule. The term "composite molecule" mentioned here means an atom cluster comprising a plurality of atoms in the broad sense.

SUMMARY OF THE INVENTION

To solve the problem described above, a method for electrically detecting a motion of nonpolar composite molecules according to a first aspect of the present invention is characterized in that in the measurement of permittivities of solids, liquids and gases containing nonpolar composite molecules, a nonuniform electric field of a different field intensity is applied to respective molecules constituting the nonpolar composite molecule, so that forces acting on dipole moments of the molecules constituting the nonpolar composite molecule are caused to differ to induce an interaction between the nonuniform electric field and the nonpolar composite molecule, thus electrically detecting the motion of the nonpolar composite molecule.

A method for electrically detecting a motion of nonpolar composite molecules according to a second aspect of the present invention is characterized in that in the first aspect, the nonuniform electric fields are generated by utilizing an electrode assembly comprising a plurality of stripe electrodes arranged in such a manner as opposed combs.

A method for electrically detecting a motion of nonpolar composite molecules according to a third aspect of the present invention is characterized in that in the first aspect, the nonuniform electric field is generated by utilizing an electrode assembly comprising stripe electrodes with a self-similar type fractal structure.

A method for electrically detecting a motion of nonpolar composite molecules according to a fourth aspect of the present invention is characterized in that in the first aspect, the nonuniform electric field is generated by utilizing an electrode assembly comprising electrodes with irregularities on their surfaces.

A method for electrically detecting a motion of nonpolar composite molecules according to a fifth aspect of the present invention is characterized in that in the first aspect, a motion of the nonpolar composite molecule is detected based on an interaction between the nonuniform electric field and a qaudrupole moment of the nonpolar composite molecule.

A method for electrically detecting a motion of nonpolar composite molecules according to a sixth of the present invention is characterized in that in the fifth aspect, an orienting energy is set at $1 \times 10^{-28}$ joule or more that is given by the product of magnitude in a quadrupole pole moment of the nonpolar composite molecule and electric field gradient of the nonuniform electric field.

A method for electrically detecting a motion of nonpolar composite molecules according to a seventh aspect of the present invention is characterized in that in the first aspect, a motion of nonpolar composite molecules is detected based on an interaction between the nonuniform electric fields and an octopole moment of the nonpolar composite molecule.

A method for electrically detecting a motion of nonpolar composite molecules according to an eighth aspect of the present invention is characterized in that in the seventh aspect, an orienting energy is set at $1 \times 10^{-28}$ joules or more that is given by the product of magnitude of an octopole pole moment in the nonpolar composite molecule and electric field gradient of the nonuniform electric field.

According to a ninth aspect of the present invention, there is proposed an electrode assembly for applying a nonuniform electric field whose intensity differs between respective molecules constituting nonpolar composite molecules in the measurement of permittivities of solids, liquids and gases containing the nonpolar composite molecule, wherein a plurality of stripe electrodes are arranged on an insulating board in such a manner as opposed combs.

An electrode assembly according to a tenth aspect of the present invention is characterized in that in the ninth aspect, the stripe electrode is thick at a proximal end and thin at a distal end.

According to an eleventh aspect of the present invention, there is proposed an electrode assembly for applying a nonuniform electric field whose intensity differs among molecules constituting nonpolar composite molecules in the measurement of permittivities of solids, liquids and gases containing the nonpolar composite molecule, wherein said electrode assembly is such that stripe electrodes with a self-similar type fractal structure are arranged on an insulating board.

According to a twelfth aspect of the present invention, there is proposed an electrode assembly for applying a nonuniform electric field whose intensity differs among molecules constituting nonpolar composite molecules in the measurement of permittivities of solids, liquids and gases containing the nonpolar composite molecule, wherein said electrodes have irregularities on their surfaces.

According to a method for electrically detecting nonpolar composite molecules utilizing a nonuniform electric field of the present invention, it is possible to obtain information on electrical responsiveness of solids, liquids and gases containing nonpolar molecules. Through the systematic study of the number of rotational vibrations of the nonpolar composite molecules contained in these substances, the magnitudes of the forces acting between the molecules and the moments of inertia of the molecules are calculated to thereby enable the cause of interactions between the nonpolar composite molecules to be sought. Further, by utilizing the present detection method in combination with differential thermal analysis or the like that is one of general thermal analytical techniques, a phase transition where the motion of nonpolar composite molecules is frozen at a certain temperature or below, such as a quadrupole alignment phase transition occurring in a solid, can be detected.

BEST MODE FOR CARRYING OUT THE INVENTION

The following is a detailed description of embodiments of the present invention with reference to the appended drawings. First, a measurement principle as a premise of the invention is explained and then the embodiments are described.

Figure 1:
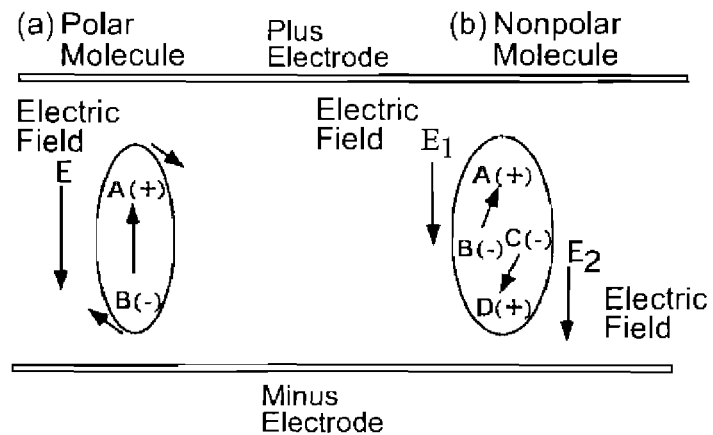
FIG. 1 is a diagram illustrating a rotation of a molecule caused by an electric field and interactions between electric fields and axes of the molecules.

FIG. 1 schematically shows interactions between electric fields and molecules. The conventional dielectric measurement method utilizing a uniform electric field generated by parallel-plate electrodes utilizes, as shown at the left side (a) of FIG. 1, an axial directional change of a molecule, as illustrated by a short arrow thereof, which is caused by an interaction between an electric dipole moment indicated by an arrow directed from B to A and an electric field E. For a polar molecule with a dipole moment, the conventional method is effective. For nonpolar composite molecules with two arrowed dipole moments $A^+B^-$ and $C^-D^+$ combined to each other with their polarities mutually reversed, as shown at the right side (b) of FIG. 1, however, forces of the electric fields acting on $A^+B^-$ and $C^-D^+$ are canceled, thus making it impossible to change the molecular direction by the electric field. In other words, in the case of utilizing a uniform electric field, it is impossible to electrically detect the motion of a nonpolar molecule.

However, if it is possible to make the electric field $E_1$ acting on the $A^+B^-$ dipole different from the electric field $E_2$ acting on the $C^-D^+$ dipole by utilizing a none-uniform-plane electrodes, a force for urging the $A^+B^-$ dipole toward a direction parallel with the electric field $E_1$ is allowed to differ from a force for urging the $C^+D^-$ dipole toward a direction inversely parallel with the electric field $E_2$, and thus the molecular axis can be rotated by the external electric fields. In general, two dipole moments coupled with mutually inversed polarities, as shown in FIG. 1, are defined as a quadrupole moment. The above-described means that an electric field change with the location (an electric field gradient) and the quadrupole moment are in an interactional situation. Consequently, by utilizing such interaction, a change in molecular axis of the nonpolar molecule, i.e., the motion of the molecule can be electrically detected.

By utilizing a further higher-order interaction, e.g., an interaction between a second order differential for a location in the electric field and an octoplole moment, it is possible to detect a motion of an even more symmetrical molecule, i.e., an electrically inert composite molecule.

Next, a description is given in some detail about a principle of the nonuniform electric field method. In the vicinity of an origin $$\vec{r}\,'=0 \qquad (1)$$

a molecule to be examined is placed and an electric charge density distribution is defined as $$\rho(\vec{r}\,') \qquad (2)$$

Further, when, in substitution for an electrode charge, a unit charge is positioned at a location $$\vec{r} \qquad (3)$$

and a potential is defined as $$\phi(\vec{r}) \qquad (4)$$

then, the following equation can be given:

$$\phi(\vec{r}) = \frac{1}{4\pi\varepsilon_0} \int \frac{\rho(\vec{r}\,')}{|\vec{r}-\vec{r}\,'|} dV' \qquad (5)$$

wherein, if $$\theta \qquad (6)$$

is defined as an angle between $$\vec{r} \qquad (7)$$

and $$\vec{r}\,' \qquad (8)$$

, then the equation:

$$\frac{1}{|\vec{r}-\vec{r}\,'|} = \frac{1}{\sqrt{r^2 + r'^2 - 2rr'\cos\theta}} \qquad (9)$$

can be given.

When this expression is expanded by the power of $$r'/r \qquad (10)$$

, then $$\frac{1}{|r-r'|} = \frac{1}{r\sqrt{1-2(r'/r)\cos\theta + (r'/r)^2}}$$
$$= \frac{1}{r}\sum (r'/r)^l P_l(\cos\theta) \qquad (11)$$

is yielded. If $$\cos\theta = x \qquad (12)$$

then, $$P_l(x) \qquad (13)$$

is the Legendre's function defined as $$P_l(x) = \frac{1}{2^l l!} \frac{d^l}{dx^l}(x^2-1)^l \qquad (14)$$

Therefore, the first several terms can be written as $$P_0(x) = 1 \qquad (15)$$

$$P_1(x) = x \qquad (16)$$

$$P_2(x) = \frac{1}{2}(3x^2 - 1) \qquad (17)$$

and $$P_3(x) = \frac{1}{2}(5x^3 - 3x) \qquad (18)$$

When this electrostatic potential is expanded around the origin $$\vec{r}\,'=0 \qquad (19)$$

then the zeroth term obtained by the expansion, in other words, a value obtained when $$l=0 \qquad (20)$$

and $$\frac{1}{|r-r'|} = \frac{1}{r} \qquad (21)$$

is set up, is given as the following expression:

$$\phi_0(\vec{r}) = \frac{1}{4\pi\varepsilon_0 r} \int \rho(\vec{r}\,') dV' \qquad (22)$$

This expression corresponds to an interaction between a unit charge positioned at $$\vec{r} \qquad (23)$$

and the total charge $$Q = \int \rho(\vec{r}\,') dV' \qquad (24)$$

Then, the first term in the series by the expansion, i.e., the one obtained when $$l=1 \qquad (25)$$

is expressed as $$\phi_1(\vec{r}) = \frac{\vec{r} \cdot}{4\pi\varepsilon_0 r^3} \int \vec{r}' \rho(\vec{r}') dV' \qquad (26)$$

This expression represents an interaction between the first derivative term (an electric field) of potential:

$$\vec{E} = \frac{\partial}{\partial x_i} \phi(\vec{r}) = \frac{\vec{r} \cdot}{4\pi\varepsilon_0 r^3} \qquad (28)$$

caused by a unit charge positioned at a location $$\vec{r} \qquad (27)$$

and a molecular charge bias (a dipole moment) expressed by $$P = \int \vec{r}' \rho(\vec{r}') dV' \qquad (29)$$

The second term in the series by the expansion, i.e., the one obtained when $$l=2 \qquad (30)$$

is expressed by $$\phi_2(\vec{r}) = \frac{\vec{r}_i \vec{r}_j}{4\pi\varepsilon_0 r^5} \frac{1}{2} \int (3r'_i r'_j - \delta_{ij} r'^2) \rho(\vec{r}') dV' \qquad (31)$$

This expression represents an interaction energy expressed by the product of the first derivative for a location of the electric field, i.e., the secondary derivative of the potential $$\frac{1}{2} \frac{\partial^2}{\partial x_i \partial x_j} \phi(\vec{r}) = \frac{1}{2} \frac{1}{4\pi\varepsilon_0} \frac{\partial^2}{\partial x_i \partial x_j} \left(\frac{1}{r}\right) = \frac{\vec{r}_i \vec{r}_j}{4\pi\varepsilon_0 r^5} \frac{1}{2} \qquad (32)$$

and a quadrupole moment $$D_{ij} = \int (3r'_i r'_j - \delta_{ij} r'^2) \rho(\vec{r}') dV' \qquad (33)$$

which is possessed by a charge distribution.

Next, the third term in the series by the expansion represents a high-order interaction energy expressed by the product of the tertiary derivative for the position of the potential, i.e., the secondary derivative of the electric field $$\frac{1}{3!} \frac{\partial^3}{\partial x_i \partial x_j \partial x_k} \phi(\vec{r}) = \frac{1}{3!} \frac{1}{4\pi\varepsilon_0} \frac{\partial^3}{\partial x_i \partial x_j \partial x_k} \left(\frac{1}{r}\right) \qquad (34)$$

and an octopole moment $$O_{ijk} = \int (5r'_i r'_j r'_k - 3r_i \delta_{ij} \delta_{jk} r^2) \rho(\vec{r}') dV \qquad (35)$$

which the electric charge distribution possesses.

According to the conventional dielectric measurement method utilizing a uniform electric field generated by parallel flat plates, the interaction between the first term in the series by the expansion of potential, i.e., the first derivative term for the location of electrostatic potential (i.e., an electric field) and a dipole moment serving to indicate the bias of a electric charge, has been utilized. According to such uniform electric field method utilizing the first term in the series by the expansion, it is impossible to electrically detect the motion of a nonpolar molecule having no dipole moment.

The rationale for the nonuniform electric field method according to the present invention is the interaction between the first derivative for the location of the electric field (i.e., an electric field gradient) in the second term in the series by the expansion of the potential and a quadrupole moment. The quadrupole moment is defined as a combination of two reversely-directed dipole moments. The second term indicates that the motion of a nonpolar molecule with a quadrupole moment can be detected electrically by utilizing a location-dependent electric field generated by none-uniform-plane electrodes, i.e., an electric field whose intensity changes between constituent molecules constituting the nonpolar composite molecule.

A further higher-order interaction, i.e., the interaction between the third term in the series by the expansion of the potential, i.e., the secondary derivative for a location of an electric field and an octopole moment becomes available by utilizing the foregoing nonuniform electrodes. In that case, it becomes possible to detect the motion of a nonpolar molecule that has such an even more symmetric property that it is electrically inert and has only the octopole moment, without any quadrupole moment.

Figure 2:
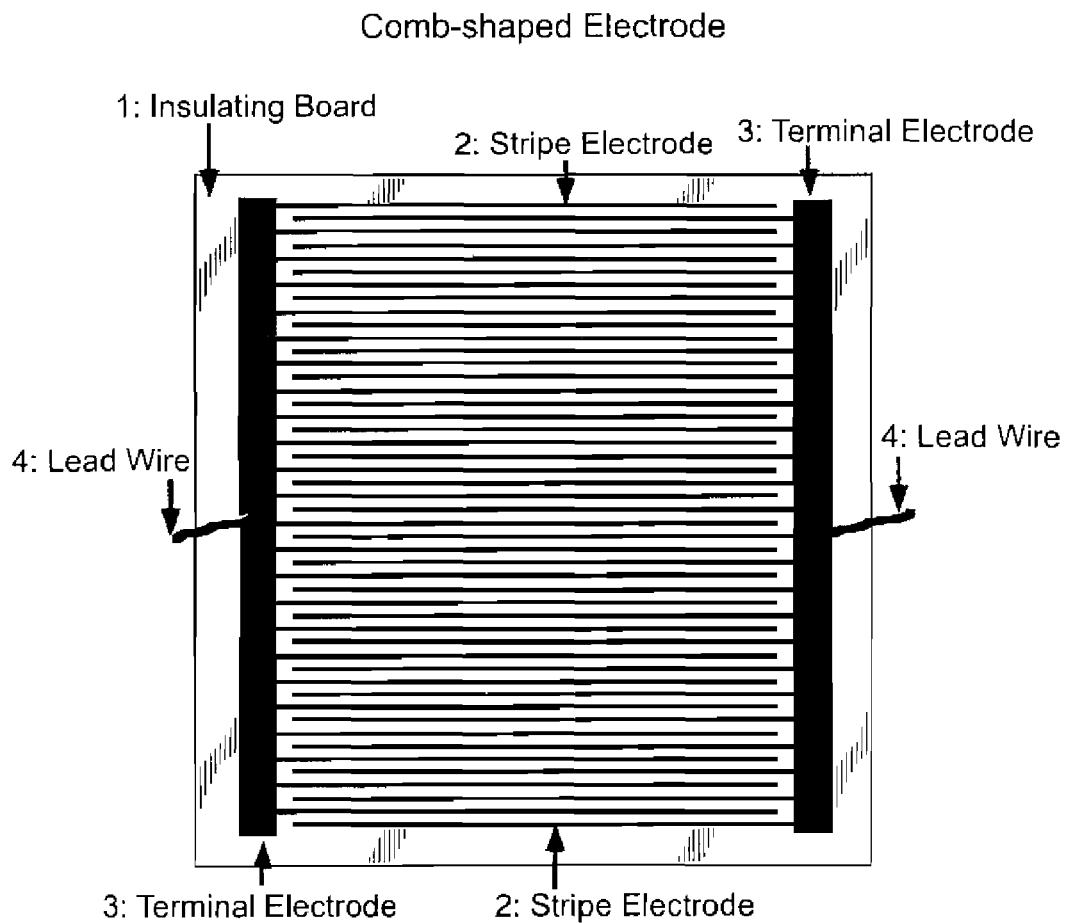
FIG. 2 is a front view of a comb-shaped electrode assembly in accordance with a first embodiment of the present invention.

As a means for generating a nonuniform electric field so that its intensity may vary among molecules constituting nonpolar composite molecules, an electrode plate having a stripe structure is employed in place of the one having a uniform-plane structure. FIG. 2 shows one example of such electrode assemblies. The electrode assembly is constructed by arranging two comb-shaped electrodes opposite to each other, said comb-shaped electrode comprising a stripe electrode made up of a plurality of linear electrodes arranged substantially in parallel, and arranged on a tabular insulating board 1 made from ceramic or glass epoxy, as shown in FIG. 2. The two comb-shaped electrodes described here are arranged so that the linear electrodes of the stripe electrodes 2 are alternately located. These comb-shaped electrodes can be fabricated by using fine processing techniques such as a photoresist technique employed generally in fabricating a printed-circuit board or a direct processing using laser.

Figure 3:
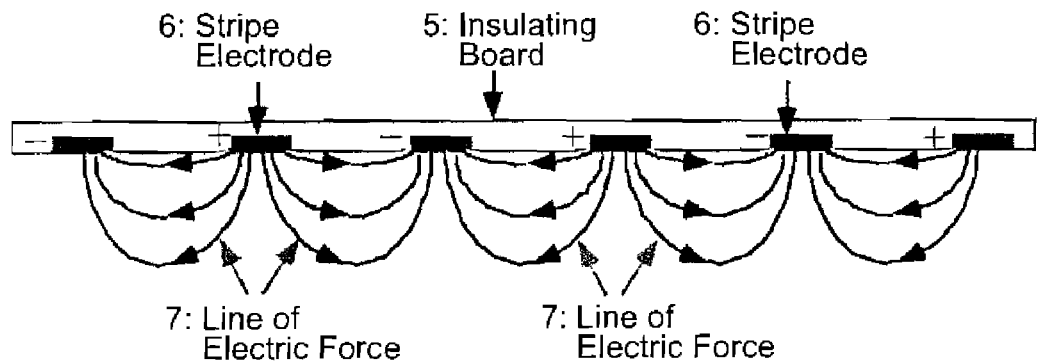
FIG. 3 is a schematic diagram illustrating electric fields that are generated by the comb-shaped electrode assembly and vary with the location.
Figure 4:
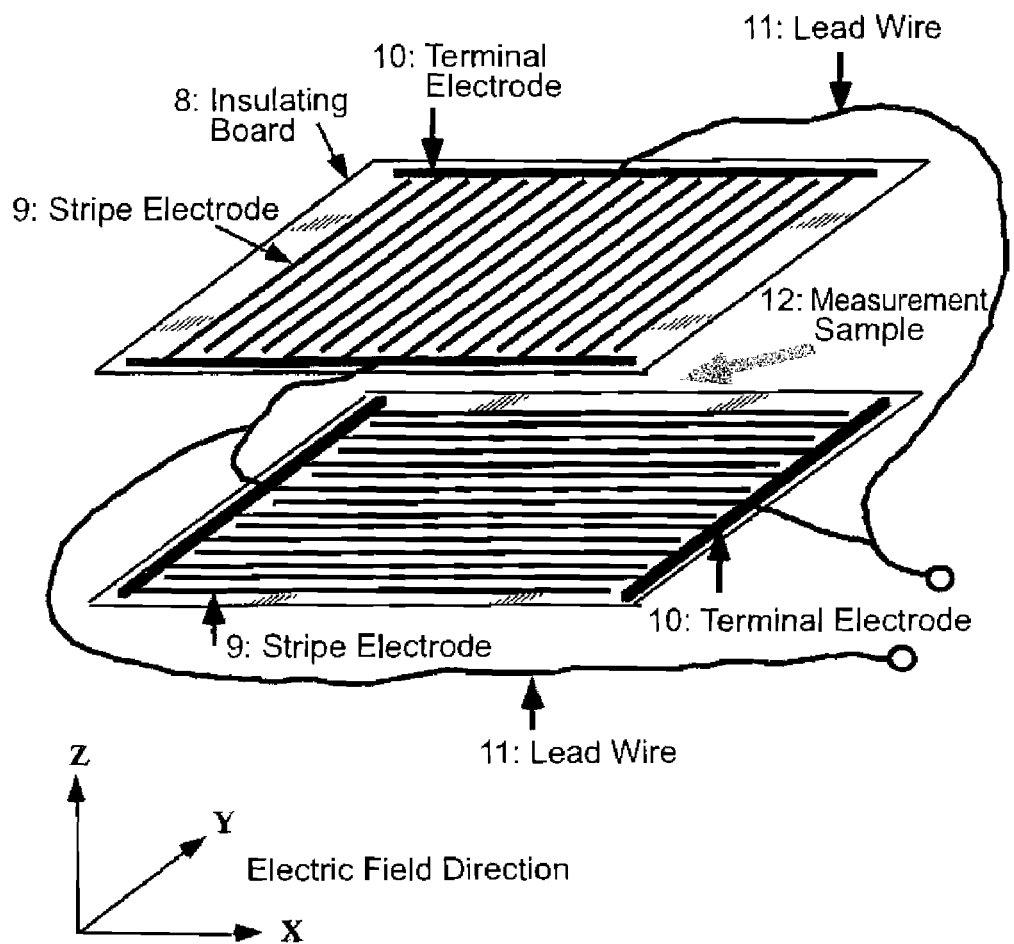
FIG. 4 is a wiring diagram in connecting the two comb-shaped electrode assemblies with one above the other.

When plus and minus voltages are alternately applied to the comb-shaped stripe electrodes 2, electric fields are, as shown in FIG. 3, varied with the location in such a fashion that the nearer to the plus or minus electrodes the stronger the electric fields becomes due to electrical flux lines 7 taking the form as if being short-circuited near the plus or minus electrodes, whereas the farther from the electrodes the weaker the electric fields becomes due to the electrical flux lines 7 going the longer way around. As shown in FIG. 4, the two electrodes are arranged so that surfaces of upper and lower stripe electrodes 9 are opposed so as to be perpendicular to each other and besides so as to be nearly parallel with each other. Then, a lead wire 11 at one side and the one at the other side of the two electrodes are connected as shown in FIG. 4 and a voltage is applied across the lead wires 11, so that an electric field gradient is formed in three directions of X, Y and Z. An extremely thin measurement sample 12 (a solid powder, a liquid and a gas) is sandwiched between the upper and lower electrodes 9 so that the thickness of the sample becomes substantially equal to an interval between the stripe electrodes 9. Then, the lead wires 11 may be connected to a capacitance meter or an LCR meter to measure a real part of the permittivity, the dielectric loss or the alternating-current conductivity.

Using the nonuniform electric field method according to the present invention, the direction of nonpolar composite molecules can be varied electrically. In other words, through the nonuniform electric field, an energy flow is generated from the electrodes, which is then turned into rotational energy of the nonpolar composite molecule to thereby allow the energy flow to be detected electrically as a variation in dielectric loss. In the nonuniform electric field method, a critical frequency of rotation of the composite molecule is detected from the frequency dependence of alternating-current impedance such as the permittivity and the dielectric losses, like in the conventional method utilizing the uniform electric field.

A time scale of a motion detectable by the Raman scattering method which has been used as a general method for analyzing a mode of the nonpolar composite molecule is in the range of $10^{11}$ seconds or less. In contrast, the present method can utilize an ordinary dielectric measuring device and hence relaxation phenomenon can be observed in a wider-range time scale of $10^3$ to $10^{10}$ seconds.

Figure 5:
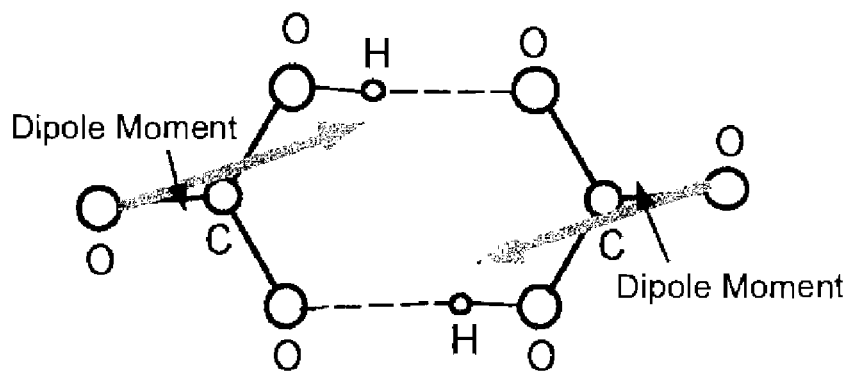
FIG. 5 is a diagram illustrating two hydrogen-bonded carbonic acid molecules in potassium hydrogen carbonate ($KHCO_3$).

Next, as an example of applications of the foregoing nonuniform electric field method, a measurement result of potassium hydrogen carbonate $KHCO_3$ will be shown. In potassium hydrogen carbonate, two carbonate molecules $HCO_3$ are coupled via two hydrogen atoms as shown in FIG. 5. These $(HCO_3)_2$ molecules have no dipole moment due to a combination of the two reversely-directed dipole moments but have a quadrupole moment as a high-order multipole moment. This substance is subjected to a structural phase transition at about 50 degrees. Therefore, at high temperature, the axes of the molecules $(HCO_3)_2$ are tilted at about 5° not horizontally but vertically in a random order. At a temperature equal to or less than the one at which the phase transition occurs, however, array alignment of the axes of the molecules occurs.

Figure 6:
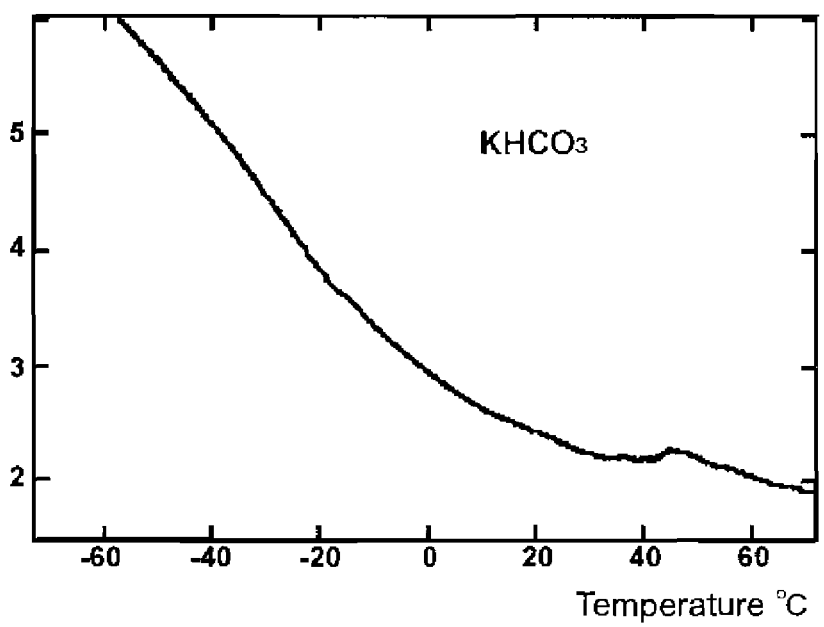
FIG. 6 is a graph of dielectric measurement data of potassium hydrogen carbonate obtained by the measurement utilizing the nonuniform electric field according to the first embodiment of the present invention, in which the abscissa and ordinate axes indicate temperature and alternating-current conductivity, respectively.

FIG. 6 shows the temperature dependence of the alternating-current conductivity corresponding to the dielectric loss of the molecules $(HCO_3)_2$ when the nonuniform electric field generated by the comb-shaped electrodes is applied. In the case of utilizing the nonuniform electric field method, a peak is observed at about 50 degrees C. This peak corresponds to a mode that is attributable to the spin of the nonpolar molecules $(HCO_3)_2$ as previously observed by the present inventers in neutron scattering (see "Dynamic of the strain-mediated phase transition in KDCO3" K. Kakurai et al., Physical Review Vol. 53, no. 10, pp 5974-5977, 1996).

In fabricating an electrode assembly for generating the nonuniform electric field, it is desirable to make intervals of the electrodes smaller, yet distances between the stripe electrodes and widths of the electrodes need to be designed, taking a response to alternating-current frequency into consideration. For low frequencies (1 KHz or less), the stripe electrodes that have intervals and widths in the order of microns or less, and lengths of a few centimeters may be employed, whereas at higher frequencies, the stripe electrodes need to be designed so as to be wider and shorter, taking an electrode inductance into consideration.

In addition, the molecules $(HCO_3)_2$ have qudarupole moments and therefore the motions of the molecules $(HCO_3)_2$ are detected based on the interactions between the nonuniform electric field and the quadrupole moments of the nonpolar composite molecules $(HCO_3)_2$. When detecting the motion of the nonpolar composite molecule having the quadrupole moment like this, the larger an orienting energy, the more precisely the motion of the molecule can be detected, said orienting energy being given by the product of magnitude of the quadrupole moment in the nonpolar composite molecule and a nonuniform electric field gradient.

For example, hydrochloric acid (HCl) having a typical dipole is possessed of a dipole moment of $1.7 \times 10^{-29}$ C·m. According to the conventional method, for example, a sample is disposed between two flat-plate electrodes arranged at an interval of 1 mm and then a voltage of 1V is applied across the electrodes to perform dielectric measurement. At this time, since the electric field between the electrodes is $10^3$ V/m, the resultant orienting energy of the hydrochloric acid molecule is $1.7 \times 10^{-26}$ joules from the product of the dipole moment and electric field.

On the contrary, magnitude of the quadrupole of a carbon dioxide gas $(CO_2)$ as a nonpolar molecule with a typical quadrupole moment is $14.3 \times 10^{-40}$ C·m$^2$. The two electrodes 2 of the present embodiment that are arranged at intervals of 1 μm so that the surfaces of the two electrode assemblies are opposed nearly parallel to each other with the linear portions of the stripe electrodes disposed orthogonal to each other. Then, when a voltage of 1V is applied across the electrodes, the intensity of the electric field becomes $10^6$ V/m. Further, a distance between a position where the intensity of the electric field is zero and a position where it is $10^6$ V/m is $10^{-6}$ m, and hence, magnitude of the electric field gradient results in $10^{12}$ V/m$^2$. At this time, the orienting energy of the carbon dioxide gas becomes $1.4 \times 10^{-27}$ joules as it is given by the product of the quadrupole moment and electric field gradient, which is large enough to be comparable to that of the dipole moment of hydrochloric acid molecule.

As described above, by making the intervals of the stripe electrodes on the order of 1 μm in the electrode assembly of the present embodiment, the orienting energy of the carbon dioxide gas molecule becomes $1.4 \times 10^{-27}$ joules, thus permitting the motion of the nonpolar composite molecule with the quadrupole moment to be detected at substantially the same level of accuracy as the level at which the conventional dielectric measurement of the hydrochloric acid molecule has heretofore been done. In the meantime, in order to ensure a certain degree of the measurement accuracy, it is preferable to select the stripe electrodes of which the intervals of the linear portions can realize $1 \times 10^{-28}$ joules or more as an orienting energy given by the product of the magnitude of the quadrupole moment in the nonpolar composite molecule and the electric field gradient in the nonuniform electric field.

Further, when electrically detecting the motion of nonpolar composite molecules that is electrically inert, having an octopole moment only, and no quadrupole moment, and thus having an extremely high symmetric property, the motion of the nonpolar composite molecule can be detected based on the interaction between the nonuniform electric field and the octopole moment of the nonpolar composite molecule by utilizing the same electrode assembly as is utilized for detecting the nonpolar composite molecule with the quadrupole moment. In that case as well, for the same reason as the discussed above, preferable stripe electrodes may be selected so that the orienting energy given by the product of magnitude of the octopole moment of the nonpolar composite molecule and the electric field gradient in the nonuniform electric field becomes $1 \times 10^{-28}$ joules or more.

Figure 7:
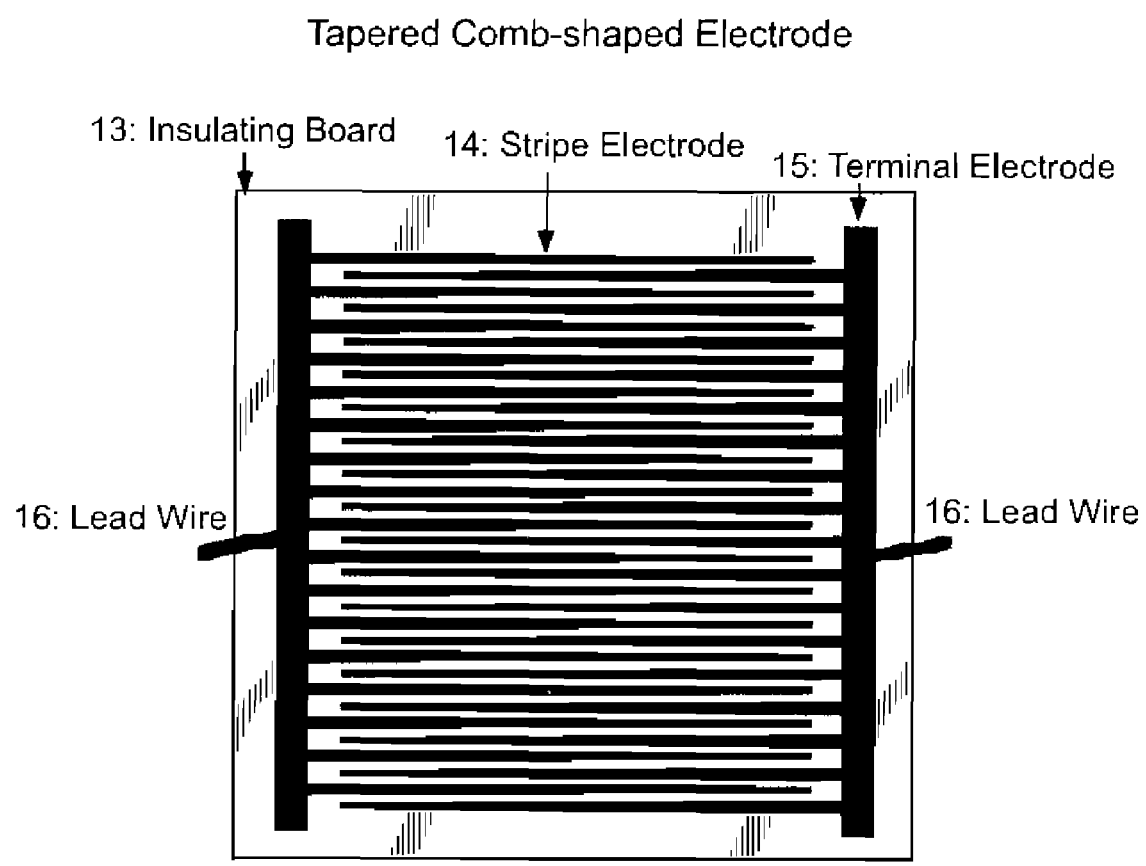
FIG. 7 is a view showing a modified comb-shaped electrode assembly, i.e., tapered comb-shaped electrodes according to the first embodiment of the present invention.

FIG. 7 shows another example of the electrode assembly employed in the first embodiment, which is a modified example of the comb-shaped electrodes in which the proximal ends of the stripe electrodes 14 are designed so as to be wider and the distal ends thereof are designed so as to be thinner in view of influence from the inductance in the electrode assembly lead wires. In this tapered comb-shaped type electrodes, a drawback that the junctions of the stripe electrodes 14 and terminal electrodes 15 are liable to be cut off when applying photo-etching or the like is improved.

As described above, the method for electrically detecting a motion of nonpolar composite molecules of the present embodiment provides the nonuniform electric field whose intensity differs between molecules constituting the nonpolar composite molecule at the time of the measurement of permittivities of solids, liquids and gases that contain the nonpolar composite molecules, whereby the motions of the nonpolar composite molecules are detected based on the interaction between the nonuniform electric field and the quadrupole moment of the nonpolar composite molecules.

Consequently, information on electric responses of solids, liquids and gases that contain nonpolar molecules can be obtained. Then, through the systematic examination of the number of rotational vibrations of the nonpolar composite molecule contained in these substances, the magnitude of the force acting between molecules and the moments of inertia of molecules are calculated to thereby permit a cause of the interactions between the nonpolar molecules to be figured out. Further, by utilizing the present detection method in combination with differential thermal analysis or the like that is one of general thermal analytical techniques, a phase transition where the motion of nonpolar composite molecules is frozen at a certain temperature or below, such as a quadrupole alignment phase transition occurring in a solid, can be detected.

Figure 8:
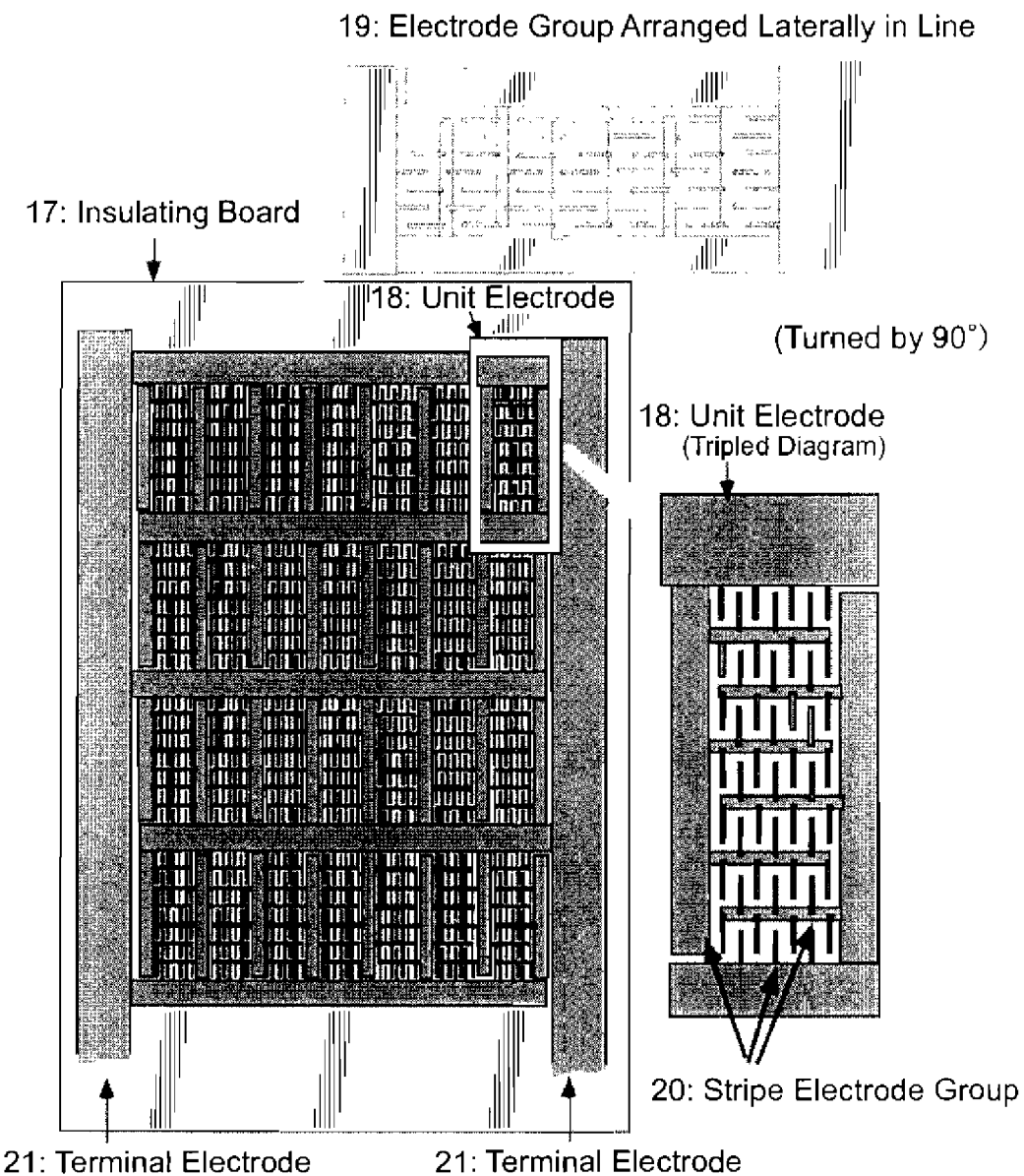
FIG. 8 is a schematic diagram showing a fractal electrode assembly according to a second embodiment of the present invention, said fractal electrode assembly generating an electric field gradient.

An electrode assembly shown in FIG. 8 is an improved type of the comb-shaped electrode assembly, in which the stripe electrodes are formed in a fractal shape. The fractal shape is called a self-similar shape, in which a shape of any part corresponds to a reduced shape of the whole. In the present embodiment, a portion shown as a unit electrode 18 represents a basic constituting unit of the electrode. The basic constituting unit that is tripled and turned by 90° forms an electrode group 19 located in the uppermost row. Further, the electrode group 19 that is tripled and turned vertically by 90° forms a group of the whole electrodes. Since the unit electrode 18 comprises minute-patterned stripe electrodes 20 each having a twice-reduced similar shape (i.e., $(1/3)^2$), the electrodes of different sizes coexists with the size differing on a scale of 1 to $3^4$ times or about 100 times. Using the recent fine processing technology, it is possible to easily make up a fractal electrode assembly with electrodes of different sizes ranging on a scale of 1 to 1,000 times.

Like a network of animal blood vessels, the fractal electrode assembly can respond to up to high frequencies due to low impedance of its thick electrodes located near a signal source, while it can suitably respond to lower frequencies due to the minuteness of the stripe electrodes similar to peripheral capillary blood vessels. The feature of the fractal electrode assembly is situated in the fact that due to the coexistence of multi-stage electrode structures where each electrode is thick at the proximal end and then becomes gradually thinner toward its distal end, an effective inductance of the stripe electrode is reduced to improve its alternating-current characteristics, thus efficiently covering a wider frequency range, using a single electrode.

Figure 9:
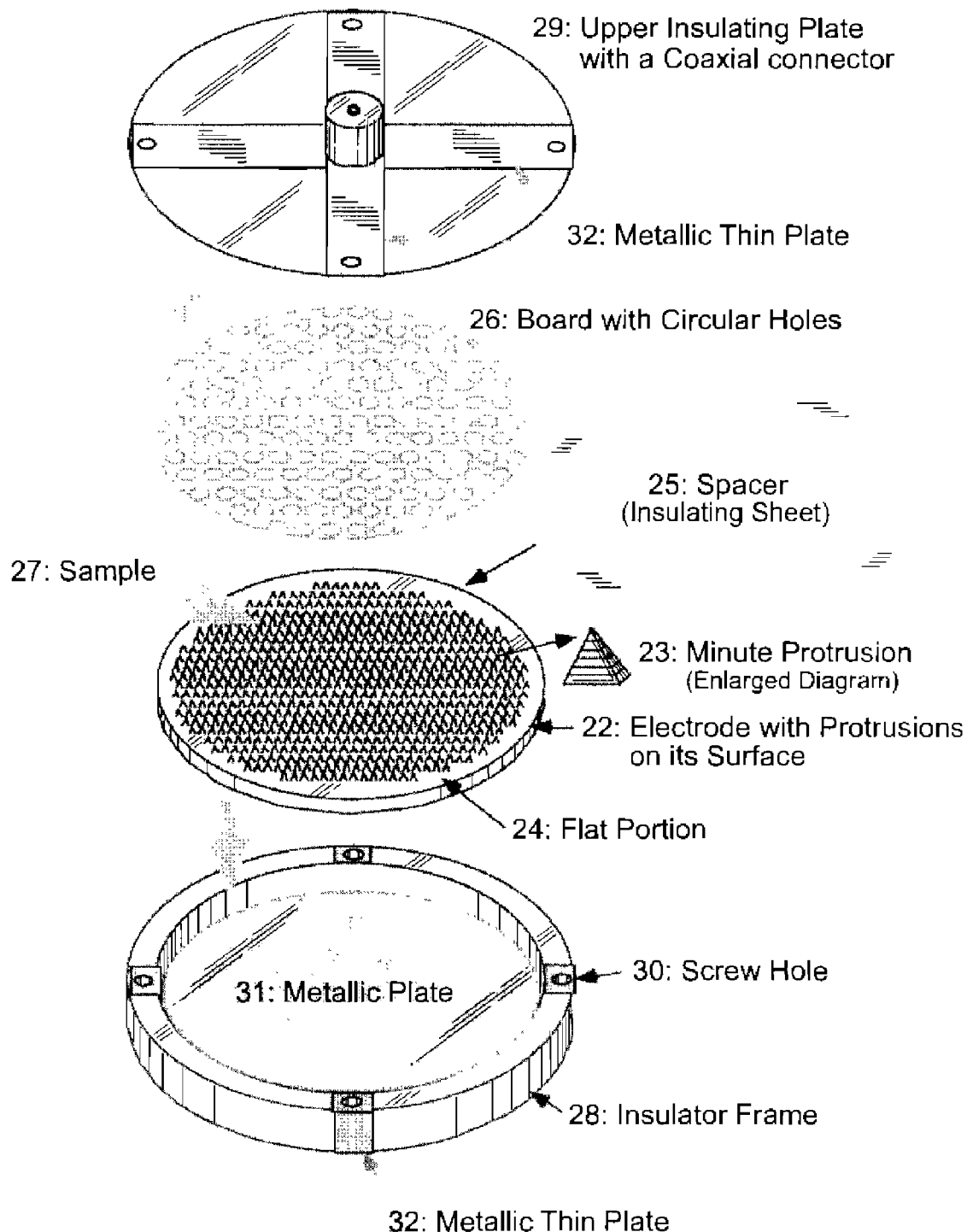
FIG. 9 is a schematic diagram showing an electrode assembly with irregularities on its surface according to a third embodiment of the present invention, said electrode assembly generating an electric field gradient.
Figure 10:
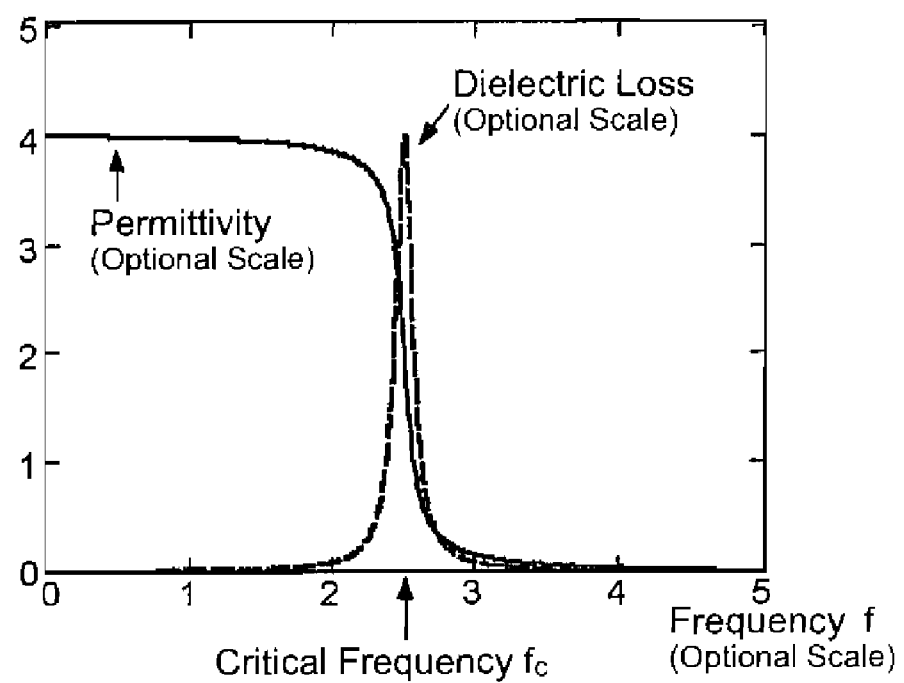
FIG. 10 is a graph showing frequency dependences of permittivity and dielectric loss according to the conventional art.

At frequencies as high as in the region of MHz, voltage change with time does not transfer up to an end of the electrode due to influence by inductance of the stripe electrode, so that the performance of the comb-shaped electrode assembly deteriorates. Accordingly, an electrode assembly comprising electrode plates with irregularities on their surface is employed for frequencies higher than a MHz frequency level. FIG. 9 illustrates one example of such type of the electrode which is processed so that minute protrusions whose widths and heights are in the order of several microns are provided thereon. This electrode can be fabricated by a horizontal type NC precise milling machine. An example shown in FIG. 9 is the electrode with the minute protrusions each having a quadrangular pyramid shape, with an apex angle 30°. The minute protrusions are formed by operating a cutting blade of the milling machine perpendicularly in a scanning manner at intervals of 20 μm. In order to form the electrode with irregularities on its surface with a high degree of accuracy, it is most preferable to employ a ruling machine used for notching a diffraction grating, or otherwise, a laser fine processing technique applied to a metallic mirrored surface.

The advantage of the electrode with irregularities on its surface is in that the inductance of the electrode itself can be extremely reduced, permitting the electrode to be employed for up to high frequencies. However, since the electric field gradient generated by the minute protrusions 23 is utilized, accuracy in laser processing and milling machining is required. As materials for the electrode, brass or phosphor bronze may be used. These materials must be, however, selected carefully so as to make the apex angle of the minute protrusion 23 as small as possible to obtain a large electric field gradient. Further, in order to avoid contact and short-circuiting between the minute protrusions 23 on the electrode 22 and the electrode 26 on an opposite side, a certain area outside of the protrusions on the metallic plate is left unprocessed to some extent as shown in FIG. 9 to form a flat portion 24 for providing a spacer (an insulating sheet) 25 made from Teflon (trademark registration) in such a manner that the spacer 25 is sandwiched therein. For the counterpart of the electrode 22 may be used the board 26 with a number of circular eyeholes formed through the metallic portion, a metallic disk 31, the electrode 22 with protrusions on its surface, etc. The board 26 is, however, the most preferable from a standpoint of hereinbelow-described impedance matching regulation at high frequencies, since an effective area of the electrode can be easily adjusted by the size and number of the eyeholes to be formed in the board 26.

These two of the electrode 22 and the board 26 are opposed with one above the other and with the electrode surface of the board 26 faced downward, while a sample powder 27 to be measured is inserted therebetween with the thickness of the sample being in the order of several microns. Then, this set is housed in an insulator frame 28 the whole of which is made from ceramic or Teflon (trademark registration). Further, the set of the electrodes (i.e., an electrode assembly) housed is held down by an insulating plate 29 with a coaxial connector so as to be fixed by screwing screws into four screw holes 30 provided in the insulator frame 28. A central line of the coaxial connector fixed to the central portion of the insulating plate 29 is coupled to the electrode of the board 26, and a ground lead outside the coaxial connector is connected to the metallic plate 31 located underneath through a metallic thin metal 32. In measuring at a high frequency region, the coaxial cable is connected to a high-frequency LCR meter to perform dielectric measurement. The board 26 with the circular eyeholes is fabricated using a glass epoxy board by the technology such as photoresist or the like in the same way as is the case with the fabrication of the comb-shaped electrode.

In the meantime, a characteristic impedance of 50Ω is generally employed in a dielectric measuring device for a MHz frequency range, and hence, diameters of the electrode 22 and board 26 as well as the size and number of the eyeholes formed in the board 26 need to be adjusted so that a capacitance of a capacitor comprising the electrode 22, the board 26 and a sample may be matched to 50Ω in impedance at a measuring frequency.

Whilst several embodiments of the invention have been described as above, the electrode assembly for generating the nonuniform electric field according to the present invention is not limited to the foregoing embodiments but various modifications are possible. For example, an electrode assembly mounted with a metallic net comprising a fine mesh may be employed.

Currently, the dielectric measurement is being extensively employed as one of means for evaluation or analysis of properties of substances contained in solids and liquids (condensed substances). The present method expands a range of target molecules detectable by the existing molecule detecting method from a polar molecule to a nonpolar molecule, and this it can be utilized as a fundamental analytical technique for solids and liquids. For example, polymeric molecule orientational order within plastic is one factor for determining its strength and electric characteristics, and therefore the conventional dielectric measurement has heretofore been successfully employed as a physical analytical technique for the polar molecule. The extension to the nonpolar molecule analytical technique according to the present invention is considered to contribute to the development of plastic materials as well. Further, it is expected that the present invention may be applied to a quantitative evaluation of an insulating body (a low-k-material) having an extremely small permittivity, which is being used in the semiconductor industry.

The invention claimed is:

1. A method for electrically detecting a motion of nonpolar composite molecules, comprising a step of providing a nonuniform electric field whose intensity differs between the molecules constituting said nonpolar composite molecules in the measurement of permittivities, as a function of frequency, of solids, liquids and gases containing said nonpolar composite molecules, so that forces acting on dipole moments of the molecules constituting the nonpolar composite molecule are caused to differ to induce an interaction between the nonuniform electric field and the nonpolar composite molecule, thus electrically detecting a rotational motion of the nonpolar composite molecule.

2. The method for electrically detecting a motion of nonpolar composite molecules according to claim 1, wherein said nonuniform electric field is generated by utilizing a plurality of stripe electrodes arranged in such a manner as opposed combs.

3. The method for electrically detecting a motion of nonpolar composite molecules according to claim 1, wherein said nonuniform electric field is generated by utilizing stripe electrodes of a self-similar type fractal structure.

4. The method for electrically detecting a motion of nonpolar composite molecules according to claim 1, wherein said nonuniform electric field is generated by utilizing electrodes with irregularities on their surfaces.

5. A method for electrically detecting a motion of nonpolar composite molecules, comprising a step of providing a nonuniform electric field whose intensity differs between the molecules constituting said nonpolar composite molecules in the measurement of permittivities of solids, liquids and gases containing said nonpolar composite molecules, so that forces acting on dipole moments of the molecules constituting the nonpolar composite molecule are caused to differ to induce an interaction between the nonuniform electric field and the nonpolar composite molecule, thus electrically detecting the motion of the nonpolar composite molecule, wherein the motion of the nonpolar composite molecules is detected based on an interaction between said nonuniform electric field and a quadrupole moment of said nonpolar composite molecules.

6. The method for electrically detecting a motion of nonpolar composite molecules according to claim 5, wherein an orienting energy given by a product of magnitude of a quadrupole moment in said nonpolar composite molecule and an electric field gradient of said nonuniform electric field is $1 \times 10^{-28}$ joules or more.

7. A method for electrically detecting a motion of nonpolar composite molecules, comprising a step of providing a nonuniform electric field whose intensity differs between the molecules constituting said nonpolar composite molecules in the measurement of permittivities of solids, liquids and gases containing said nonpolar composite molecules, so that forces acting on dipole moments of the molecules constituting the nonpolar composite molecule are caused to differ to induce an interaction between the nonuniform electric field and the nonpolar composite molecule, thus electrically detecting the motion of the nonpolar composite molecule, wherein the motion of the nonpolar composite molecule is detected based on an interaction between said nonuniform electric field and an octopole moment of said nonpolar composite molecule.

8. The method for electrically detecting a motion of nonpolar composite molecules according to claim 7, wherein an orienting energy given by a product of magnitude of an octopole moment of said nonpolar composite molecule and an electric field gradient of said nonuniform electric field is $1 \times 10^{-28}$ joules or more.

* * * * *